United States Patent [19]

Laurenzo et al.

[11] Patent Number: 4,889,954

[45] Date of Patent: Dec. 26, 1989

[54] AMINE OXIDE PROCESS

[75] Inventors: Kathleen S. Laurenzo; Dennis P. Bauer, both of Baton Rouge, La.

[73] Assignee: Ethyl Corporation, Richmond, Va.

[21] Appl. No.: 213,685

[22] Filed: Jun. 30, 1988

[51] Int. Cl.[4] ............................................ C07C 135/02
[52] U.S. Cl. ...................................................... 564/298
[58] Field of Search .......................................... 564/298

[56] References Cited

U.S. PATENT DOCUMENTS

| 4,247,480 | 1/1981 | Murata et al. | 564/298 |
| 4,748,275 | 5/1988 | Smith et al. | 564/298 |

Primary Examiner—Douglas W. Robinson
Assistant Examiner—Raymond J. Henley, II
Attorney, Agent, or Firm—Joseph D. Odenweller

[57] ABSTRACT

Tertiary amines are converted to amine oxides in high conversion and at a faster rate by including dialkylcarbonate in the reaction of the tert-amine with aqueous hydrogen peroxide. Ascorbic acid can be used as a co-catalyst.

21 Claims, No Drawings

AMINE OXIDE PROCESS

BACKGROUND

It has long been known to make amine oxides by reaction of tertiary amines with aqueous hydrogen peroxide with or without a co-solvent. Catalysts reported to promote the reaction are octacyanomolybdate or iron salts (U.S. Pat. No. 4,565,891), carbon dioxide (U.S. Pat. No. 4,247,480), alkali metal polyphosphate and bicarbonate (U.S. Pat. No. 3,333,000), sodium salt of ethylenediamine tetraacetic acid (U.S. Pat. No. 3,432,555) and salicylic acid (Chem. Abst. 102(18) 151229 g).

Nitrosamines are formed as minor by-products in the conventional preparation of tert-amine oxides using aqueous hydrogen peroxide. Although the amount of nitrosamine is very small, on the order of parts per billion (ppb), this small amount renders the amine oxide unsuitable in many applications that involve human contact. This is because nitrosamines are reported to be carcinogenic and/or mutagenic. Amine oxides have properties that would make them very useful in shampoo, hair conditioners, dish and laundry detergent, fabric softeners and the like. Hence a need exists for a method for making tert-amine oxides in high conversion and yield and at a fast reaction rate and at the same time producing a tert-amine oxide product that has reduced levels of nitrosamines. The present invention provides such a process.

SUMMARY

According to the present invention the reaction of tert-amines with hydrogen peroxide is promoted by including a small amount of dialkylcarbonate in the reaction mixture.

DESCRIPTION OF THE PREFERRED EMBODIMENT

A preferred embodiment of the invention is a process for making an amine oxide, said process comprising reacting a tertamine capable of forming an amine oxide with aqueous hydrogen peroxide in the presence of a catalytic amount of a dialkylcarbonate.

The process is applicable to any tert-amine capable of forming an amine oxide. These are well known to organic chemists. They include amines which do not have a hydrogen atom bonded to the amine nitrogen atom. Such amines include trialkylamines; triarylamines; triaralkylamines; mixed alkyl-aryl, alkyl-aralkyl, aryl-aralkyl or alkyl-aryl-aralkylamines; tricycloalkylamines; dialkyl-cycloalkylamines; diaryl-cycloalkylamines; cyclic amines, e.g. N-methyl piperidine, N,N'-dimethyl piperazine, pyridine, 2-methyl pyridine, N-methyl pyrrolidine, N-methylpyrrolidone, N-ethyl morpholine and the like.

In a more preferred embodiment the tert-amine has the formula $R^1R^2R^3N$ wherein $R^1$ is an alkyl group containing 1-30 carbon atoms and $R^2$ and $R^3$ are alkyl groups containing 1-30 carbon atoms, cycloalkyl groups containing 5-12 carbon atoms, aryl groups containing 6-12 carbon atoms, aralkyl groups containing 7-12 carbon atoms or any two of the R groups can join to form a carbocyclic or hetrocyclic ring or all three of the R groups may participate to form a pyridine ring.

The process is applicable to any of a broad range of tert-amines such as butyldimethylamine, hexyldimethylamine, isobutyl dimethylamine, 2-ethylhexyl dimethylamine, octyldimethylamine, decyldimethylamine, dodecyldimethylamine, tetradecyl dimethylamine, hexadecyldimethylamine, eicosyldimethylamine, docosyldimethylamine, triacontyldimethylamine, tributylamine, butyldiethylamine, isobutyldiethylamine, decylbutylethylamine, hexadecylhexylmethylamine, eicosyldibutylamine, trioctylamine, tridodecylamine, dieicosylethylamine, ditriacontylmethylamine, N,N,-dimethylaniline, N-methyl-N-dodecylaniline, cyclopentyldimethylamine, cyclohexyldimethylamine, dicyclohexylmethylamine, cyclododecyldimethylamine, diphenylbutylamine, p-tolyl diethylamine, α-naphthylbutylmethylamine, benzylbutylmethylamine, α-methylbenzylbutylmethylamine, 4-butylbenzyloctylmethylamine, dibenzylbutylamine, 4-pentyl-benzyldibutylamine, N-butylmorpholine, N-methylmorpholine, N-methylpiperidine, N-dodecylpiperidine, N-octadecylpiperidine, N-triacontylpiperidine, N-methylpiperazine, N-butylpiperazine, N-octylpiperazine, N-phenylpiperidine, N-benzylpiperidine, N-cyclohexylpiperidine, pyridine and the like.

In a more preferred embodiment the tert-amine is a trialkylamine having the structure $R^1R^2R^3N$ wherein $R^1$, $R^2$ and $R^3$ are primary alkyls having 1-30 carbon atoms. Representative examples of these include, but are not limited to, trimethylamine, tri-n-pentylamine, tri-n-dodecylamine, n-octadecyl di-(n-butyl)amine, n-eicosyl di-(n-decyl)amine, n-triacontyl-n-dodecylmethylamine and the like.

In a still more preferred embodiment $R^1$ is a primary alkyl group containing 6-22 carbon atoms and $R^2$ and $R^3$ are independently selected from methyl and ethyl groups.

In a further preferred embodiment $R^1$ is a mainly linear primary alkyl containing 8-20 carbon atoms and $R^2$ and $R^3$ are methyl groups. By "mainly linear" is meant that over 50 percent, more preferably 70 percent and most preferably 90 percent of the $R^1$ groups are linear alkyls containing 8-20 carbon atoms.

Examples of this preferred embodiment are octyldimethylamine, decyldimethylamine, dodecyldimethylamine, tetradecyldimethylamine, hexadecyldimethylamine, octadecyldimethylamine, eicosyldimethylamine and mixtures thereof.

In another more preferred embodiment of the invention, both $R^1$ and $R^2$ are independently selected from primary alkyls containing 6-22 carbon atoms and $R^3$ is a methyl or ethyl group.

In a highly preferred embodiment $R^1$ and $R^2$ are independently selected from mainly linear primary alkyl groups containing 8-20 carbon atoms and $R^3$ is methyl. Examples of this highly preferred embodiment are dioctylmethylamine, didecylmethylamine, didodecylmethylamine, ditetradecylmethylamine, dihexadecylmethylamine, dioctadecylmethylamine, dieicosylmethylamine, decyloctylmethylamine, dodecyloctylmethylamine, tetradecyldecylmethylamine, hexadecyltetradecylmethylamine, octadecylhexadecylmethylamine, eicosyldodecylmethylamine and the like including mixtures thereof.

Any aqueous hydrogen peroxide can be used including those containing 3-90 percent $H_2O_2$. Preferably the hydrogen peroxide is 20-70 weight percent active $H_2O_2$. When the tertamine is linear $C_{8-20}$ alkyl dimethylamine, it is preferred that the aqueous hydrogen peroxide be about 20-40 weight percent $H_2O_2$ to avoid gel formation. Alternatively, more concentrated hydrogen peroxide can be used and additional water co-fed to maintain a saturable reaction mixture. Likewise, co-solvents such as lower alcohol, e.g., isopropanol, isobutanol and the like, can be used to avoid gelation.

The amount of hydrogen peroxide should be at least a stoichiometric amount. A useful range is about 1–5 moles of $H_2O_2$ and more preferably 1–1.5 mole of $H_2O_2$ per mole of tert-amine. A highly preferred amount is about 1.05–1.3 moles of $H_2O_2$ and especially about 1.1–1.2 moles of $H_2O_2$ per mole of tert-amine. Any excess $H_2O_2$ remaining after the reaction can be destroyed by the addition of a reducing agent or a peroxide decomposition catalyst such as manganese dioxide.

When the process is conducted using a di-linear alkyl methylamine, the process can be carried out using more concentrated aqueous hydrogen peroxide such as about 45–70 weight percent hydrogen peroxide. When the di-linear alkyls contain up to about 6–12 carbon atoms each, the reaction mixture will remain substantially gel free. When the di-linear alkyls contain 14 or more carbon atoms the reaction mixture will set up to a dry flakeable solid on cooling.

The reaction can be conducted over a wide temperature range. The temperature should be high enough to cause the reaction to proceed at a reasonable rate but not so high as to lead to decomposition of the reactants or products. A useful temperature ranqe is from about 0–100° C.. A more preferred temperature range is about 30–90° C.. A still more preferred temperature range is about 40–75° C.. Most preferably the reaction is conducted at about 50–75° C.. In this temperature range the reaction is quite rapid. Excellent results have been achieved at about 65° C..

The reaction rate is catalyzed by dialkylcarbonates. These include dimethylcarbonate, diethylcarbonate, methylisobutylcarbonate, dioctylcarbonate ethyldodecylcarbonate, didecylcarbonate and the like. The preferred carbonates are di-primary alkylcarbonates and more preferably· di-linear-alkylcarbonates. Still more preferred are the di-lower alkylcarbonates in which the alkyls are primary alkyls of 1–4 carbon atoms. The most preferred carbonates are dimethylcarbonate, diethylcarbonate and methylethylcarbonate and especially dimethylcarbonate.

The amount of dialkylcarbonate can vary over a wide range. It is required that the amount of dialkylcarbonate in the reaction mixture be an amount which causes the reaction to proceed at a faster rate than the rate achieved without the addition of dialkylcarbonate. In other words there should be at least a promoter amount of dialkylcarbonate. The upper limit of dialkylcarbonate is not critical. A useful concentration is about 0.05–5.0 weight percent based on the weight of the initial tertamine. Even more dialkylcarbonate can be used, e.g. 10 weight percent or more but this does not appear to give any advantage.

One way to add the dialkylcarbonate is to dissolve the dimethylcarbonate in the tert-amine. Alternatively, although it is fairly insoluble in water, a small amount can be dissolved in any water added to the reaction vessel. If a co-solvent such as an alcohol is used, the dimethylcarbonate can be dissolved in the co-solvent.

In another preferred embodiment the dialkylcarbonate promoter is used in combination with an ascorbic acid cocatalyst. The amount of ascorbic acid should be a promoter amount. A useful concentration of ascorbic acid is about 0.005–10 weight percent based on the initial tert-amine reactant. A preferred concentration of ascorbic acid is about 0.05–5 weight percent. A more preferred concentration is about 0.1–2 weight percent and a most preferred concentration of ascorbic acid is 0.2–1 weight percent. The use of an ascorbic acid cocatalyst is not essential.

Instead of ascorbic acid, salts of ascorbic acid can be used such as ammonium or alkaline metal salts. Likewise isomeric forms of ascorbic acid are included in the scope of the invention.

The following example shows a method for carrying out the process by feeding the aqueous hydrogen peroxide to a reactor containing the tert-amine and promoter.

EXAMPLE 1

In a glass reaction vessel was placed 250 g of dodecyldimethylamine (1.17 moles) and 12.5 g (5.0 weight percent) dimethylcarbonate. The mixture was stirred at 65° C. and 83.6 g of 50 weight percent aqueous hydrogen peroxide was added over a 75minute period at 65–70° C.. Water was added as required to prevent gelling (total water 563 g). Stirring was continued at 65° C. for an additional 105 min. (3 hours total reaction time). Conversion to dodecyldimethylamine oxide was 97 percent. Further analysis for nitrosamines using a Thermal Energy Analyzer by an adaptation of the method described in Krull, I.S. et. al., Anal. Chem. 51 1706 (1979) gave the following results in parts per billion.

| N—nitrosodimethylamine | 23 ppb |
| N—nitrosomethyldodecylamine | 107 ppb |

A conventional oxidation conducted at 65° C. to the same conversion without the dimethylcarbonate would contain much higher nitrosamine levels.

EXAMPLE 2

In a glass reaction flask was placed 250 g dodecyldimethylamine and 1.25 g (0.5 weight percent of amine). The mixture was stirred and 83.6 g 50 weight percent aqueous hydrogen peroxide was added over 36 minutes at 60–68° C.. A total of 563 g of water was co-fed to prevent gelling. At one hour from start the amine conversion was 80 percent complete and at 2 hours it was 92 percent complete. The reaction mixture was let stand at room temperature overnight. The conversion was then 98 percent. The product contained 84 ppb N-nitrosodimethylamine and 117 ppb N-nitrosomethyldodecylamine.

EXAMPLE 3

This reaction was conducted in the same manner as Example 2 except that 1.25 g (0.5 weight percent of amine) of diethylcarbonate was used as the catalyst. Time to feed hydrogen peroxide was 53 minutes. Conversion was 84 percent at 3 hours from start and 90 percent at 5 hours from start. After standing several days at room temperature the conversion had increased to 94 percent. The product contained 184 ppb N-nitrosodimethylamine and 246 ppb N-nitrosomethyldodecylamine.

EXAMPLE 4

In a reaction flask was placed 250 g dodecyldimethylamine, 1.25 g dimethylcarbonate and 1.25 g L ascorbic acid. The mixture was stirred and heated to 65° C.. Then 83.6 g 50 percent aqueous hydrogen peroxide was added over 1 hour at 65–67° C.. Water was periodically added to prevent gel (total 563 g water). Stirring was continued for 2 hours at 63–67° C. at which time conversion of amine was 95 percent. After standing overnight at room temperature, conversion was 99 percent by NMR. The product contained 38 ppb N-nitrosodimethylamine and 212 ppb N-nitrosomethyldodecylamine.

EXAMPLE 5

This is a baseline run without catalyst for comparative purposes.

In a reaction flask was placed 250 g dodecyldimethylamine. Then 84.2 g of 50 percent aqueous hydrogen peroxide was added slowly to the stirred mixture at 60–67° C. (mostly 63–67° C.) over a 88-minute period. Water was added periodically to prevent gel (total water 585 g). The mixture was stirred at 60–67° C.. After 7 hours from start of hydrogen peroxide feed the conversion was still not complete. The reaction was let stand overnight at room temperature. The mixture was re-heated to 65° with stirring and the reaction was continued. After 4 more hours the amine conversion was 99 percent. The product contained 418 ppb N-nitrosodimethylamine and 296 ppb N-nitrosomethyldodecylamine. These are substantially higher than those obtained in the presence of a dialkyl carbonate promoter.

We claim:

1. A process for making an amine oxide, said process comprising reacting a tert-amine selected from the group consisting of trialkylamine, triarylamine, triaralkylamine, mixed alkyl-aryl, alkylaralkyl, aryl-aralkyl or alkyl-aryl-aralkyl amine, tricycloalkyl amine, dialkyl-cycloalkylamine, diaryl-cycloalkylamine, N-$C_{1-30}$ alkyl piperidine, N,N'-dimethyl piperazine, pyridine, 2-methyl pyridine, N-methylpyrrolidine, N-methylpyrrolidone and N-$C_{2-4}$ alkyl morpholine which is capable of forming an amine oxide with 1–5 moles of aqueous hydrogen peroxide per mole of said tert-amine in the presence of a catalytic amount in the range of from 0.05 to 5.0 weight percent based on the weight of the initial tert-amine of a dialkylcarbonate in which each alkyl group contains up to 12 carbon atoms.

2. A process of claim 1 wherein said tert-amine is a trialkylamine.

3. A process of claim 2 wherein said dialkylcarbonate is a di-$C_{1-4}$ alkylcarbonate.

4. A process of claim 3 wherein said trialkylamine is a $C_{6-22}$ alkyl di-$C_{1-2}$ alkylamine.

5. A process of claim 4 wherein said trialkylamine is dodecyldimethylamine.

6. A process of claim 4 wherein said trialkylamine is tetradecyldimethylamine.

7. A process of claim 4 wherein said trialkylamine is hexadecyldimethylamine.

8. A process of claim 3 wherein said trialkylamine is a di-$C_{6-22}$ alkyl $C_{1-2}$ alkylamine.

9. A process of claim 8 wherein said trialkylamine is didecylmethylamine.

10. A process of claim 2 conducted at a temperature of 25–75° C..

11. A process of claim 10 wherein said dialkylcarbonate is dimethylcarbonate.

12. A process of claim 11 wherein said tert-amine is a $C_{6-22}$ alkyl di-$C_{1-2}$ alkylamine.

13. A process of claim 12 wherein said tert-amine is dodecyldimethylamine.

14. A process of claim 12 wherein said tert-amine is tetradecyldimethylamine.

15. A process of claim 12 wherein said tert-amine is hexadecyldimethylamine.

16. A process of claim 11 wherein said tert-amine is a di-$C_{6-22}$ alkyl $C_{1-2}$ alkylamine.

17. A process of claim 16 wherein said tert-amine is didecylmethylamine.

18. A process of claim 1 conducted in the presence of an ascorbic acid co-catalyst.

19. A process of claim 18 wherein said tert-amine is a $C_{6-22}$ alkyl di-$C_{1-2}$ alkylamine.

20. A process of claim 18 wherein said tert-amine is di-$C_{6-22}$ alkyl $C_{1-2}$ alkylamine.

21. A process for producing an amine oxide which comprises oxidizing a tertiary amine of the formula

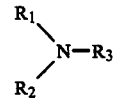

wherein $R_1$ is an alkyl group containing 1–30 carbon atoms and $R_2$ and $R_3$ are each selected from the group consisting of an alkyl group containing 1–30 carbon atoms, a cycloalkyl group containing 5–12 carbon atoms, an aryl group containing 6–12 carbon atoms and an aralkyl group containing 7–12 carbon atoms wherein any two of $R_1$, $R_2$ and $R_3$ can be joined to form a heterocyclic ring, with aqueous hydrogen peroxide, in the presence of a catalytic amount of a di-linear-alkylcarbonate; wherein the hydrogen peroxide is present in a range of from 1–5 moles of hydrogen peroxide to every 1 mole of tertiary amine present and the alkyl carbonate is present in at least a concentration range of from 0.05 to 5.0 weight percent based on the weight of the initial tertiary amine.

* * * * *